United States Patent [19]
Atkins

[11] Patent Number: 5,531,720
[45] Date of Patent: Jul. 2, 1996

[54] I.V. STARTING KIT AND COUPLING, AND METHOD

[76] Inventor: Stephen L. Atkins, 1018 Blair Ave., Modesto, Calif. 95350

[21] Appl. No.: 272,688

[22] Filed: Jul. 8, 1994

[51] Int. Cl.⁶ .................................................. A61M 39/10
[52] U.S. Cl. ............................................ 604/280; 604/238
[58] Field of Search .................................. 604/167, 283, 604/280, 238

[56] References Cited

U.S. PATENT DOCUMENTS

| | | |
|---|---|---|
| 4,617,012 | 10/1986 | Vaillancourt . |
| 4,655,762 | 4/1987 | Rogers ..................... 604/283 |
| 4,834,719 | 5/1989 | Arenas ..................... 604/283 |
| 4,842,591 | 6/1989 | Luther . |
| 4,935,010 | 6/1990 | Cox et al. . |
| 4,952,206 | 8/1990 | Ibanez et al. ............. 604/238 |
| 4,981,469 | 1/1991 | Whitehouse et al. . |
| 4,998,927 | 3/1991 | Vaillancourt . |
| 5,031,675 | 7/1991 | Lindgren . |
| 5,078,689 | 1/1992 | Keller . |
| 5,078,694 | 1/1992 | Wallace . |
| 5,080,654 | 1/1992 | Picha et al. . |
| 5,085,645 | 2/1992 | Purdy et al. . |
| 5,098,396 | 3/1992 | Taylor et al. . |
| 5,104,381 | 4/1992 | Gresl et al. . |
| 5,139,483 | 8/1992 | Ryan . |
| 5,167,648 | 12/1992 | Jepson et al. ............. 604/283 |
| 5,176,653 | 1/1993 | Metais . |
| 5,211,634 | 5/1993 | Vaillancourt . |
| 5,242,393 | 9/1993 | Brimhall et al. ......... 604/283 |
| 5,292,308 | 3/1994 | Ryan ......................... 604/283 |
| 5,295,969 | 3/1994 | Fischell et al. . |
| 5,324,188 | 8/1994 | Inoue et al. ............... 604/283 |
| 5,332,515 | 6/1994 | Karas et al. ............... 604/283 |

*Primary Examiner*—Paul J. Hirsch
*Attorney, Agent, or Firm*—Joseph E. Gerber

[57] ABSTRACT

A kit for starting an I.V. is disclosed, as is a coupling for preventing blood and fluids from spilling out of the kit's catheter. The kit is comprised of a catheter portion, a coupling portion and a flesh piercing portion. The cannula portion includes a cannula having a hub. The coupling portion is comprised of first and second tubular portions, and a septum bound integrally therebetween. The flesh piercing portion is comprised of a needle and a handle. The method disclosed includes the steps of lodging the first tubular portion of a resilient coupling into the hub of a catheter; driving a guide needle axially through the coupling and catheter; driving the coupling and catheter into a vein; and withdrawing the guide needle from the catheter and coupling. Although blood flows into the catheter, it is prevented from flowing beyond the self-sealing septum.

23 Claims, 4 Drawing Sheets

I.V. STARTING KIT AND COUPLING, AND METHOD

BACKGROUND OF THE INVENTION

1. Field of the Invention

The present invention relates generally to apparatus for intravenous (I.V.) infusion and effusion of blood, bodily fluids and medications, and it more specifically relates to a method and apparatus for the initial insertion of an I.V. catheter and for secure coupling of various I.V. apparatus thereto.

2. Description of the Related Art

One of riskiest procedures modern health care workers are asked to perform is starting I.V.'s. The common current practice is to drive a guide needle carrying a cannula into a patient's vein, and then to withdraw the guide needle, leaving the cannula in place. Upon withdrawal of the guide needle, the blood, under normal venous pressure, fills the cannula and has the natural tendency to flow out of the cannula's proximal end. If unimpeded, blood will continue to flow from the cannula until the health care worker couples the cannula to such I.V. apparatus as an I.V. line, a syringe or a heparin lock.

As the prevalence of AIDS, hepatitis and other blood-borne diseases is now higher than ever, and as health care workers are acutely aware of the special risks of working with blood, successful installation of a cannula in a vein commonly triggers an awkward scramble wherein, with the finger of one hand, the worker attempts to plug the flow of blood from the cannula or to press on the vein, and with the remaining hand attempts to grasp and align the intended I.V. apparatus and to couple it with the cannula. In the meantime, the guide needle is often hastily discarded, sometimes simply by being stuck into a mattress or dropped to the floor.

Daily, workers such as emergency room nurses may have to start as many as two dozen or more I.V.'s and, in a single hospital, more than several hundred may be required in any given day. Although workers commonly take the precaution of wearing rubber gloves to avoid contact with inevitably spilled blood, gloves are an insufficient barrier when working with sharp, contaminated needles, especially in the emergency room environment where the medical histories of patients are often completely unknown.

When conventional methods and equipment such as those described above are employed, each I.V. start presents a separate health-risking event. Indeed, even at best, these methods and equipment result in the necessity of clean-ups which, if they were avoidable, would at least lighten the workload of hospital staff.

Many devices for preventing back-flow in I.V. apparatus are known. And, several may be useful for starting I.V.'s, as well. Examples include the catheter adapter and valve disclosed in U.S. Pat. No. 5,085,645 issued to Purdy, et al. in 1992; and, the one-way septum and valve assembly shown in U.S. Pat. No. 4,842,591 issued to Luther in 1989. However, although such devices have now been available for some time, their use is has not been widely adopted. One reason may be that the moderate mechanical complexity of these disposable items makes them a bit more expensive than is desirable. Further, health care workers are somewhat more resistant to changing procedures and equipment than may be reasonable, but in any case, this stubbornness in the profession may continue to prevent adoption of such unfamiliar improvements.

Simpler constructions include U.S. Pat. No. 5,078,689 issued to Keller in 1992; and, U.S. Pat. No. 5,295,969 issued to Fischell, et al. in 1994. But, these are adapted to effusion of larger fluid volumes and, even if scaled-down are not well suited for use as peripheral I.V.'s.

A relatively simple I.V. catheter having a resilient valve therewithin is shown in U.S. Pat. No. 5,098,396 issued to Taylor, et al. in 1992. However, the valve of the Taylor, et al. device appears somewhat less than secure because its design would cause it to fail open rather than to fail closed. Further, although hands-free once locked, the Taylor, et al. valve is not automatic; it requires manipulation each time its orientation is changed. Yet further, the valve of the Taylor et al. device is not at all compatible with the relatively standard structure of the most commonly used catheters. Thus, for the industry and the profession to adopt its use, its unique cooperating hub and compression ring would also be required. In contrast, it would seem much more expedient for all concerned if a valve or equivalent element compatible with the shape and dimensions of most ubiquitously-used peripheral I.V. catheter structure were available.

Further, one drawback of all of the foregoing devices is that they provide but a single means for fluid containment; no backup or fail-safe mechanism is inherent in those designs. Thus, it would be beneficial if a peripheral I.V. catheter included means for secondary containment in case the primary fluid-sealing element began to leak.

SUMMARY OF THE INVENTION

The peripheral I.V. starting kit of the present invention is adapted to overcome the above-noted shortcomings and to fulfill the stated needs. In sum, the kit includes three portions, a catheter portion, a coupling portion and a flesh piercing portion. The catheter portion comprises a tubular cannula with an open, blunt distal end, and a hub securely affixed to the cannula's proximal end, the bore of the hub being wider than that of the cannula. The coupling portion comprises a cylindrical, preferably tubular, distal portion, a proximal tubular portion and a resilient, pierceable, self-sealing septum between the cylindrical and tubular portions. The flesh piercing portion comprises a handle with an elongate, rigid piercing element projecting distally therefrom. The handle and piercing element are such that when the piercing element is driven through the coupling portion's septum and through the cannula's bore such that the handle is received in the coupling portion's tubular portion, the piercing element's sharpened point protrudes a short distance beyond the cannula's open distal end.

In sum, the method of the invention is for introducing an I.V. catheter into a vein while preventing blood from flowing from the I.V. catheter. The steps of the method include: (1) lodging a resilient coupling of the type described above into the hub of the catheter; (2) driving the above piercing means axially through the coupling and catheter such that the tip of the piercing means projects from the cannula's distal end; (3) driving the piercing means and the cannula into a vein; (4) withdrawing the piercing means from the catheter and coupling. Although blood flows into the catheter, it is prevented from flowing beyond the self-sealing septum. A further aspect of the method is to engage an element of I.V. apparatus having hub and needle portions with the coupling. The hub of the element of I.V. apparatus is seated securely and sealingly within the tubular portion's bore, and the needle portion of the element of I.V. apparatus breaches the septum, thus bringing the bore of the element of I.V. apparatus into fluid communication with a vein.

It is a primary object of the present invention to provide a very safe, simple and inexpensive I.V. starting kit which frees a health care worker's hands after the catheter is introduced into a patient's vein.

It is a further object of the present invention to provide an I.V. starting kit which includes a septum portion which permits the kit's catheter to be coupled with various elements of I.V. apparatus without spilling blood.

Yet another object of this invention is to provide an I.V. starting kit which includes an element which, at once, acts as a septum and a coupling.

Yet a further object of the present invention is to provide a coupling for an I.V. catheter wherein the coupling includes a primary seal at an integral septum and a secondary seal where its rim engages the element of I.V. apparatus to which it is attached.

Still a further object of the present invention is to provide a septum able to be extremely easily retrofitted to the hubs of nearly all catheters currently being used in peripheral I.V.'s.

And, it is also an object of the present invention to provide a combination septum and coupling device having primary and secondary seals constructed to permit a user to observe when the first seal has begun to fail, while leakage is prevented by the second seal.

Another object of the present invention is to accomplish with a simple, inexpensive one-piece unit, able to act as a septum, a double and a fluid-tight coupling, what others have only achieved with more complex, expensive or cumbersome-to-use devices.

Yet a further object of the invention is to provide an I.V. catheter which, between I.V. sessions, is small enough remain comfortable to a patient.

Still further objects of the inventive kit, coupling and method disclosed herein will be apparent from the drawings and following detailed description thereof.

DESCRIPTION OF THE PREFERRED EMBODIMENT

Figure 1:
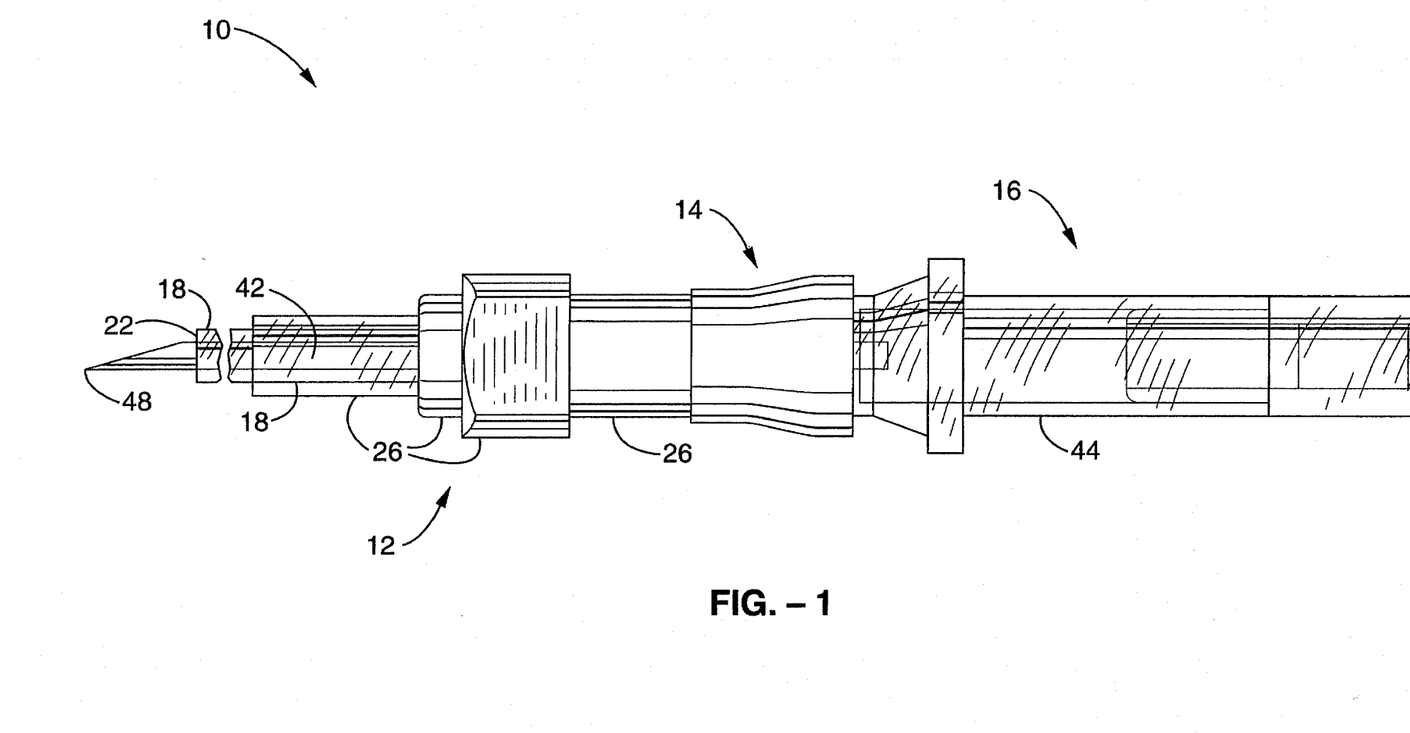
FIG. 1 is a plan view of the I.V. starting kit of the invention.
Figure 2:
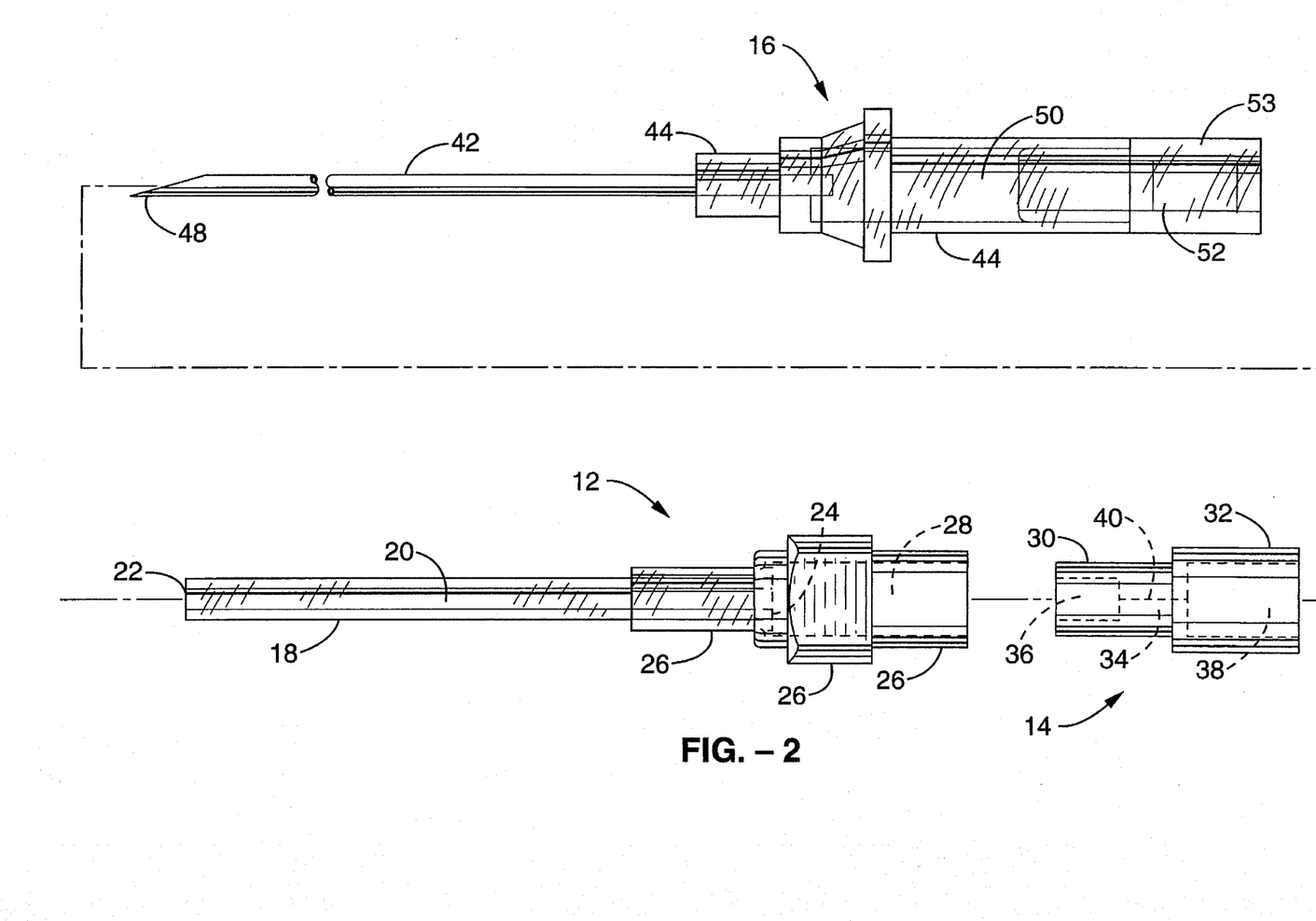
FIG. 2 is an exploded plan view of the elements of the kit of FIG. 1.

Referring now specifically to the drawings, FIG. 1 shows the inventive I.V. starting kit which is generally identified herein with reference numeral 10. As is clear from FIG. 2, I.V. starting kit 10 is comprised of three primary portions: a catheter portion 12; a coupling portion 14; and, a flesh piercing portion 16. Catheter, coupling and piercing portions 12, 14 and 16 have a common axis of rotational symmetry. It is with reference to this common axis that several of the below-identified elements are described as being coaxial.

Catheter portion 12 first includes an elongate, tubular, cannula 18 having a linear bore 20 therethrough. When constructed and dimensioned to be best suited for starting peripheral I.V.'s, cannula 18 is preferably about one inch long, or so, with an outside diameter dimensioned appropriately for receipt within the vein into which it is intended to be received. Cannula 18 is preferably constructed of plastic of a type well suited for use in medical applications. Those having a transparent or translucent character are particularly convenient. Polyethylene, polypropylene, polycarbonate, acrylic and polyvinylchloride may suffice; and, even metallic constructions may perform satisfactorily.

The distal end 22 of cannula 18 is open and blunt. As can be seen from the drawing figures, distal end 22 is cut at a ninety-degree angle. The opposing proximal end 24 of cannula 18 is securely bound into hub 26; this may be accomplished in a number of ways well known in the art.

Hub 26 is rigid and tubular. Plastics, and metals such as stainless steel, may be used in hub 26's construction. Such cannula and hub combinations are currently commercially available from many sources.

Hub 26 has a bore 28 which is coaxial with, and in fluid communication with, cannula 18's bore 20. However, hub 26's bore 28 is of a greater diameter than cannula bore 20. Further, the shape and dimensions of bore 28 preferably approximate those of the female slip portion of a conventional luer lock; although, in the context of this invention, bore 28 is not intended to receive a male luer fitting. Here, bore 28 receives coupling portion 14.

Luer fittings, both male and female, when discussed in the context of this invention, will be understood to have standardized shapes and dimensions known to those skilled in the art.

Coupling portion 14 is comprised of a first tubular portion 30 and a second tubular portion 32, with a septum 34 therebetween. In the preferred construction of coupling portion 14, first and second tubular portions 30 and 32, and septum 34, are integral with one another, being molded as a single unit from a durable, resilient, elastomeric material. Any one of a variety of natural or synthetic moldable elastomers known in the art to be suitable for such uses may suffice. And, as explained below, a translucent elastomer is preferred.

In a preferred configuration of coupling portion 14, first tubular portion 30 has a cylindrical outer surface, and a concentric, cylindrical inner bore 36. Bore 36 is coaxial with, and in fluid communication with hub 26's bore 28 and, therefore, with cannula bore 20. The outside diameter and wall thickness of first tubular portion 30 should be such as to assure that at least the distal end of portion 30 is snugly and securely received within hub 26's bore 28. To assure such a fit, in addition to the shapes and dimensions of the mating elements, certain properties of the elastomeric material of which coupling portion 14 is fashioned should also be considered. Ultimately, the frictional bond between first tubular portion 30's outer surface and the surface of bore 28 should be sufficient to retain catheter portion 12 and coupling portion 14 in secure engagement during normal use. However, in the preferred embodiment of the invention, an adhesive layer (not shown) is employed to provide yet a stronger bond between the mating surfaces of first tubular portion 30 and bore 28.

Figure 4:
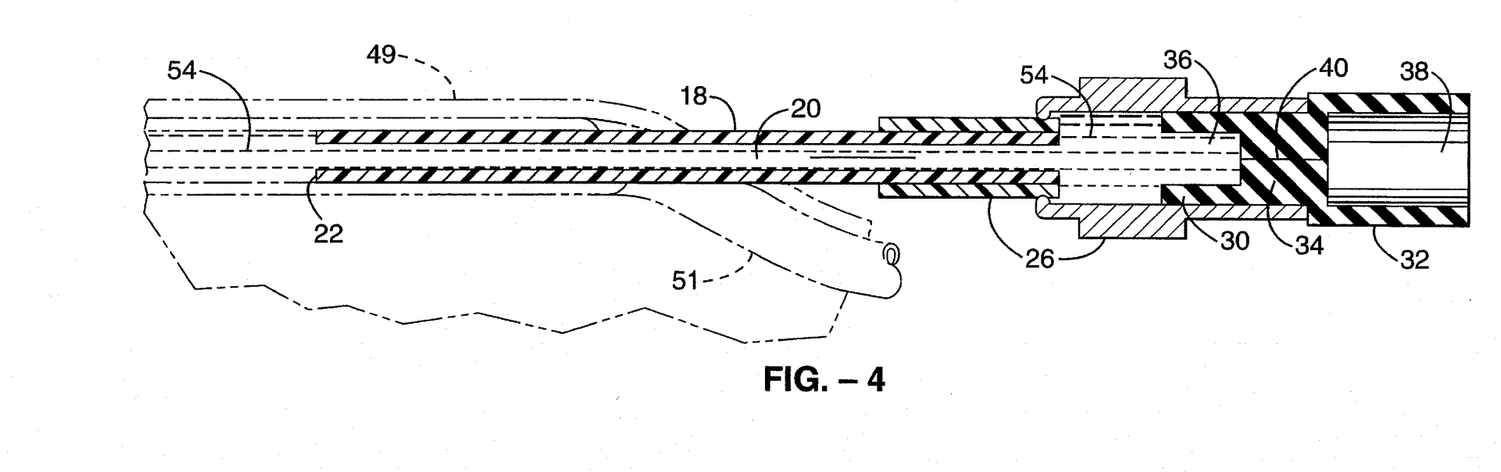
FIG. 4 is a cross-sectional view of the catheter portion of the kit in place in a vein, with the coupling portion of the invention preventing blood from flowing out of the catheter portion's hub.

Second tubular portion 32 has a cylindrical outer surface, and a concentric, cylindrical inner bore 38. Bore 38 has a larger diameter than, and is coaxial with, bore 36 of first tubular portion 30. However, bores 36 and 38 are not normally in fluid communication with one another because first and second tubular portions 30 and 32 are separated by septum 34. This is best illustrated in FIG. 4 where it can be seen that the proximal end of first tubular portion 30 meets the distal end of second tubular portion 32, and septum 34 is an integral, substantially solid plug-like portion separating the respective bores 36 and 38 thereof.

Coupling portion 14 may be constructed such that septum 34 is primarily part of the proximal end of first tubular portion 30 or primarily part of the distal end of second tubular portion 32, the former being preferred herein and having been chosen for illustration in the drawing figures. As a further alternative, septum 34 may be fashioned as an integral, substantially solid plug-like portion in the adjoined ends of both first and second tubular portions 30 and 32. As yet a further alternative, the entire bore of first tubular portion 30 could be plugged, thereby effectively substituting a substantially solid cylinder for first tubular portion 30, resulting in the entire distal end of coupling 14 acting as the septum of the invention.

Figure 3:
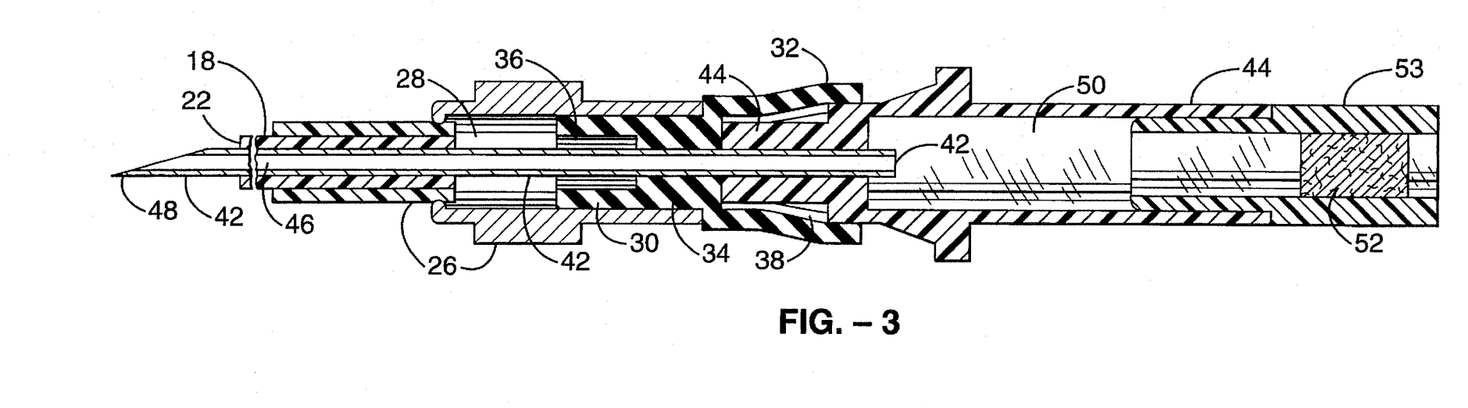
FIG. 3 is a cross-sectional view of the kit of FIG. 1.

Septum 34 has an axial channel 40 therethrough. Whatever the configuration of the septum region of coupling portion 14, coupling portion 14 may be initially manufactured with its septum intact, i.e. unpierced. However, as is evident from FIGS. 3 and 4, once kit 10 is for the first time fully assembled for use, channel 40 will result.

Septum 34, being constructed of the same resilient, elastomeric material as the rest of coupling 14, is pierceable with an instrument such as hollow hypodermic needle, a solid stylet, or the like, and yet is self-sealing once the piercing instrument is withdrawn. Septum 34 should be thick enough to re-seal securely after being pierced, and preferably durable enough to withstand repeated piercing without losing its self-sealing quality.

While a secure fit between hub 26 and first tubular portion 30 is essential, coupling portion 14's construction should be such that the septum region, however configured, is not unduly compressed or constricted after assembly. Ultimately, the septum should be easily pierceable, yet compressed sufficiently to maintain its self-sealing quality. But, the septum should neither be compressed so tightly as to cause a piercing instrument to bind unduly, nor to dislodge coupling portion 14 from its seating within hub 26 upon withdrawal.

It should be understood that when septum 34 is pierced, bores 36 and 38 are not necessarily caused to be in fluid communication with one another. Rather, as will appear further below, any piercing instrument breaching septum 34 has access to bore 36 of first tubular portion 30, and to bores 28 and 20 of hub 26 and cannula 18, respectively; but, any fluid in those bores is prevented from flowing to bore 38 of second tubular portion 32 by septum 34's ability to form a secure seal around any thin, cylindrical piercing element.

In the example of the preferred embodiment of the invention disclosed herein, the bore diameter and outside diameter of second tubular portion 32 are greater than those of first tubular portion 30. The ultimate outer diameter of second tubular portion 32 is not critical; however, the wall thickness and inner diameter of second tubular portion 32 should be suited to provide a secure frictional grip upon the various apparatus to which portion 32 is intended to be mated. One such apparatus is kit 10's flesh piercing portion 16.

Flesh piercing portion 16 of kit 10 is preferably comprised of a guide needle 42 and a needle handle 44. Guide needle 42 is of a conventional hypodermic design, having a linear central bore 46, and a sharp beveled point 48 adapted to piercing flesh. Needle handle 44 is preferably rigid and hollow, having a bore 50 in fluid communication with needle bore 46. The distal end of handle 44 should be shaped and dimensioned so as to seat snugly within bore 38 of second tubular portion 32 when kit 10 is in the fully assembled state shown in FIG. 1. A fluid-absorbent plug 52 fashioned of cotton, or the like, is lodged in the proximal end of handle 44's bore 50.

Guide needle 42 is preferably fashioned of steel, as is conventional. Needle handle 44 is preferably transparent or translucent, and may be fashioned of any suitable plastic such as polypropylene, polyethylene, polycarbonate, polyvinylchloride or acrylic. Guide needle 42 and handle 44 must be securely bound in fluid-tight relation to one another; this may be accomplished in several ways well-known in the art.

Guide needle 42's length should be such that when it is driven through septum 34 into cannula 18's bore 20 to where handle 44 meets second tubular portion 32 in snug, seating relation therewith, guide needle 42's sharpened point 48 protrudes a short distance beyond cannula 18's blunt first end 22. And, guide needle 42's diameter should be just slightly smaller than the diameter of cannula 18's bore 20. These needle-cannula relationships may be most expediently accomplished by first choosing the length and diameter of the needle needed for the intended purpose, and then choosing the appropriate cannula 18 to house the chosen guide needle 42.

It should be understood that, for some purposes, hollow guide needle and handle, 42 and 44, may be replaced with a similarly-dimensioned solid stylet and handle; but, this does not depart from the spirit of the invention.

In use, the inventive I.V. starting kit 10 is stored in the nested configuration illustrated in FIG. 1. Starting an I.V. with kit 10 is accomplished in much the same manner as with previously available devices. That is, guide needle 42's point 48 is positioned on the skin 49 above intended vein 51, and then guide needle 42 and cannula 18 are driven into vein 51 together. The snug fit of needle handle 44 into bore 38 of second tubular portion 32 helps keep portions 12, 14 and 16 together as a unit, and helps prevent guide needle 42 from being driven backward into cannula bore 20 during this insertion procedure.

Once cannula 18 is properly positioned within vein 51, blood 54 flows under its normal pressure up through needle bore 46 into needle handle 44. As blood becomes visible in handle 44's bore 50, correct cannula placement is assured and the entire flesh piercing portion 16 of kit 10 may be withdrawn. Fluid-absorbent plug 52 prevents blood 54 from passing out of the proximal end of handle 44.

At this point, blood has also advanced up through cannula bore 20 and would normally spill out of hub 26 if a typical septum-less I.V. starting kit were being used. However, coupling portion 14's self-sealing septum 34 prevents blood from passing beyond first tubular portion 30's bore 36.

Both of the health care worker's hands are now freed for attending to other tasks and, in the meantime, there is no danger of blood being spilled. One task of immediate concern is proper disposal of flesh piercing portion 16 which, by virtue of the use of kit 10, can now be attended-to in a safe and unhurried manner. Another task of immediate concern is setting up the I.V. and, for the purpose of attaching an I.V. line to catheter and coupling portions 12 and 14 which remain inserted in the patient's vein, a particular common element identified herein as blunt needle 56 is employed.

Blunt needle 56 has a thin, elongate, distally-disposed axial tip 58 in fluid communication with bore 60 within its frusto-conical hub 62. Blunt needle 56's hub 62 is proximally divergent and dimensioned so that its outer surface mates sealingly with bore 38 of second tubular portion 32. The inner surface of blunt needle hub 62 may conveniently have the shape and dimensions of a female luer slip fitting, thus enabling blunt needle 56 to mate with any apparatus having a male luer fitting.

Figure 5:
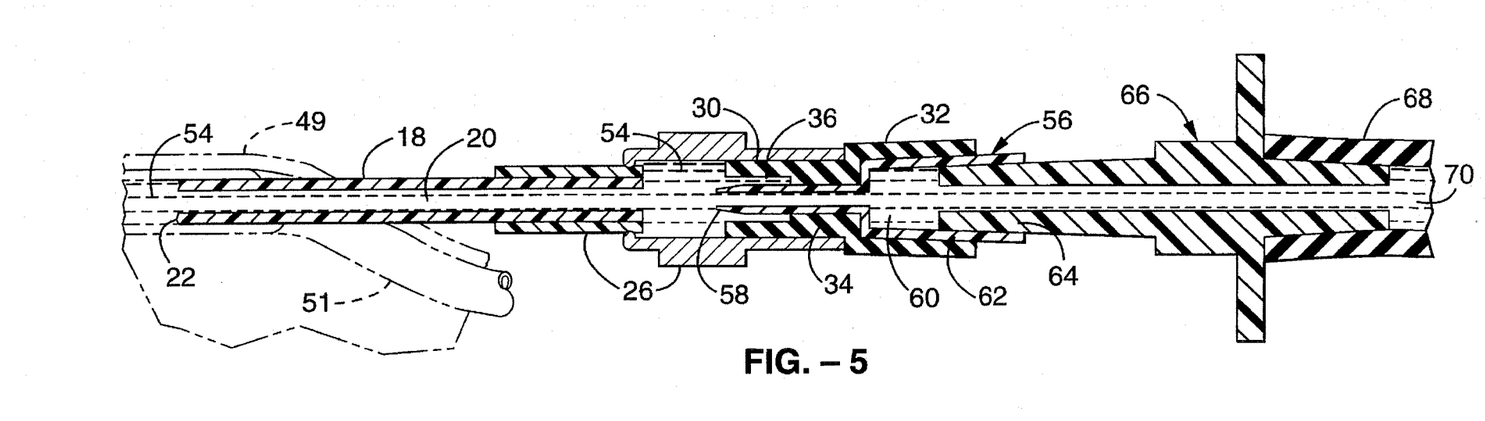
FIG. 5 is a cross-sectional view of the catheter and coupling portions of the invention mated with an irrigating tip fitted to a luer slip coupling on an I.V. line.
Figure 6:
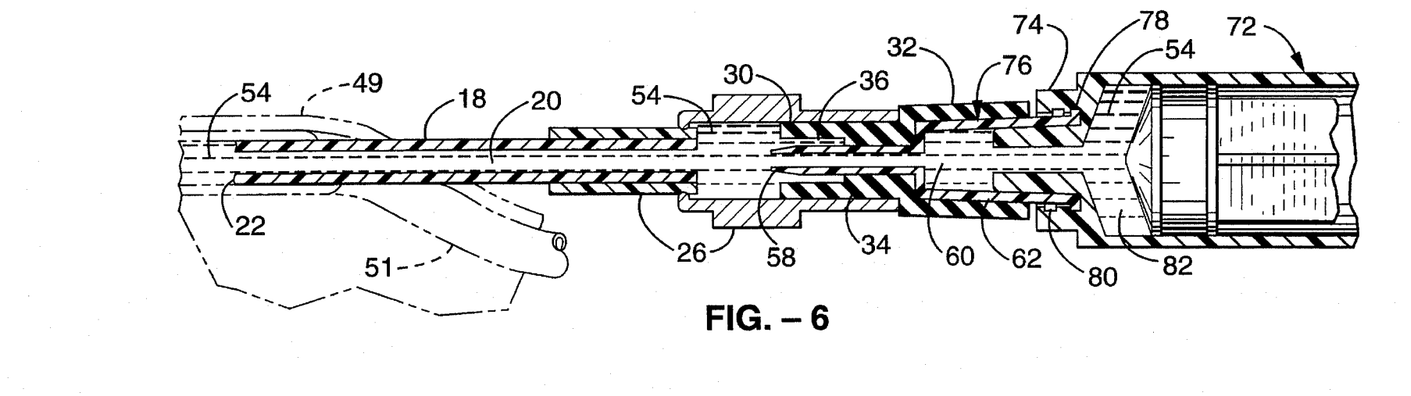
FIG. 6 is a cross-sectional view of the catheter and coupling portions of the invention mated with an irrigating tip fitted to a luer lock coupling on a syringe.

Any of a number of different commonly available pieces of I.V. apparatus may be used as blunt needle 56. The one used for example herein and shown in FIGS. 5 and 6 is a particular type of blunt needle which is of a unitary construction and fashioned of transparent rigid plastic. However, blunt needles constructed entirely of metal and of a combination of metal and plastic are well known, and are expected to work satisfactorily in practicing the invention. Actually, any common hypodermic needle of limited length may suffice, as long as the outer surface of its hub mates with the surface of bore 38 of second tubular portion 32. But, needles having sharpened beveled tips tend to reduce the service life of septum 34.

Continuing the explanation of the use of the invention, and referring specifically to FIG. 5, blunt needle 56 is mated with the standard male luer slip tip 64 of a winged coupling 66 at the terminus of an I.V. line 68. Then, tip 58 of blunt needle 56 is driven through previously-formed channel 40 in septum 34, and therebeyond, to a point where tip 58's distal end resides distal to septum 34 and preferably within bore 28 of hub 26. At this point, hub 62 seats within and mates sealingly with bore 38 of second tubular portion 32. Once so assembled, the lumen 70 of I.V. line 68 is in fluid communication with vein 51.

Once in place in vein 51, coupling portion 14 facilitates mating yet other apparatus to catheter portion 12, as well. Due to the configuration of coupling portion 14, practically any I.V. element or I.V.-compatible apparatus which can engage the hub of an appropriately-sized blunt needle may be coupled into secure fluid communication with vein 51. For example, as shown in FIG. 6, one such apparatus is syringe 72. Syringe 72 has a distal male luer lock 74 fitted with an alternative blunt needle 76 having standard luer lock tabs 78 engaging syringe 72's luer lock threads 80. Alternative blunt needle 76 mates sealingly with coupling portion 14, thus placing syringe 72's bore 82 in fluid communication with vein 51.

Fluid communication of any I.V.-related apparatus with vein 51 may be terminated by simply withdrawing blunt needle 56 from coupling 14, and no appreciable quantity of blood or I.V. fluid will pass septum 34 in so doing.

If constructed properly, even repeated insertions and withdrawals of blunt needles are unlikely to cause septum 34, the primary seal of coupling portion 14, to fail. But, in case such septum failure nevertheless occurs while a blunt needle is engaged, the configuration of coupling portion 14 provides yet a secondary seal and a fail-safe against blood and/or fluid spills. That secondary seal is between the inner surface of bore 38 of second tubular portion 32 and the outer surface of the hub (e.g. 62) of any blunt needle engaged therewith. Thus, if the primary seal at septum 34 begins to leak, the blood or fluid will tend to creep between the mating surfaces of hub 62 and second tubular portion 32. And, especially in the case of a leakage of blood, which would cause the most concern, that blood will be very visible if coupling portion 14 was manufactured from the preferred translucent elastomer discussed above. However, as rigid hub 62 is proximally divergent, and as resilient second tubular portion 32 is not, the constrictive force of second tubular portion 32 upon hub 62 will be greater toward these elements' respective proximal rims. Thus, in case of septum 34's failure, blood or fluid will only creep far enough between the mating surfaces of hub 62 and portion 32 to be visible, but not so far as to cause a risk to anyone's health by spilling. And, in that case, it will quickly be apparent that catheter portion 12 should be withdrawn from the patient and replaced, along with its coupling portion 14 and the blunt needle (e.g. 56) engaged therewith.

The configuration of coupling portion 14 also provides two areas wherein resilient gripping friction is exerted against inadvertent or otherwise unintended axial withdrawal of engaged instruments such as flesh piercing portion 16 or blunt needle 56. As above, these frictional gripping areas reside between a piercing instrument and septum 34, and where the outer surface of hub 62, or the distal end of handle 44, meets the inner surface of bore 38 of second tubular portion 32.

Coupling portion 14, yet further provides mechanical support for, and a resilient link between, catheter portion 12 and any I.V.-related element, thereby reducing the likelihood of breakage of any of the coupled apparatus in the case of, say, a restless patient. It should be noted that flexibility in the coupled apparatus is maximized when a coupling portion configured as that shown in FIGS. 3 through 6 is employed. Specifically, when constructed such that septum 34 is disposed toward the proximal end of first tubular portion 30, and a bore 36 of substantial diameter, distal to septum 34, is maintained, the needle portion of a blunt needle is more likely to pivot in septum 34 than to break, when apparatus coupled thereto is subjected to lateral force. However, such advantage would not be realized in the case of a blunt needle having such a lengthy needle portion that its tip projects into bore 20 of cannula 18.

Further, coupling portion 14's resilient construction and relatively narrow diameter cause minimal discomfort to a patient who happens to lie upon it, or to roll over upon it.

And, finally, between I.V. treatments, clotting in catheter portion 14 is prevented by simply drawing up a small volume of an appropriate concentration of heparin solution into a syringe, and coupling that syringe with catheter and coupling portions 12 and 14 as shown in FIG. 6. Once that heparin solution is deposited into and permitted to diffuse throughout the blood standing in contiguous bores 20, 28 and 36 of cannula 18, hub 26 and first tubular portion 30, clotting is prevented until the next I.V. treatment. This avoids the use of the bulky and uncomfortable heparin lock apparatus currently in common use for the same purpose. Thus, patient comfort is substantially increased when only the catheter and coupling portions 12 and 14 remain in place between I.V. treatments.

The foregoing detailed disclosure of the inventive kit 10 is considered as only illustrative of the preferred embodiment of, and not a limitation upon the scope of, the invention. Those skilled in the art will envision many other possible variations of the structure disclosed herein that nevertheless fall within the scope of the following claims. For example, although coupling portion 14 is preferably of a unitary construction, it may alternatively be assembled from two or more subcomponents adhesively bound together, without departing from the spirit of the invention.

And, alternative uses for this inventive kit may later be realized. For example, although the preferred embodiment of kit 10 disclosed herein is dimensionally best suited for starting peripheral I.V.'s, larger or smaller versions may be used for various purposes. Such purposes may include infusion and effusion of all manner of fluids to and from the body, whether or not the purpose is for intravenous communication. And, uses beyond the scope of the medical, dental, veterinary and related arts is also possible. Accordingly, the scope of the invention should be determined with reference to the appended claims, and not by the examples which have herein been given.

I claim:

1. A one-piece, leak-preventing coupling in an I.V.-starting catheter's hub having a vein engaging cannula, wherein said hub is directly contiguous with said catheter's vein-engaging cannula the coupling comprising:
   a. a first resilient tubular portion;
   b. a second resilient tubular portion integral with, and in coaxial relation with, said first tubular portion; and,
   c. a resilient, pierceable, self-sealing septum between, and integral with, said first and second tubular portions.

2. The coupling of claim 1, wherein said first tubular portion has an outside diameter smaller than said second tubular portion's outside diameter.

3. The coupling of claim 1, wherein said second tubular portion includes means for resiliently engaging a blunt needle's hub.

4. The coupling of claim 3, further including means for creating a secondary seal at said blunt needle's hub, said secondary seal being operable to contain leakage caused by failure at said septum.

5. The coupling of claim 4, further including means for permitting a visible indication of leakage of said septum.

6. The coupling of claim 1, wherein said first tubular portion is shaped and dimensions for secure receipt within a female luer slip fitting.

7. The coupling of claim 1, wherein said second tubular portion is shaped and dimensioned for secure receipt of a male luer slip fitting.

8. The coupling of claim 1, wherein said second tubular portion is shaped and dimensioned for secure receipt of a male luer slip fitting having an axially and distally-extending needle portion.

9. A one-piece, resilient, fluid conduit coupling comprising:
   a. a resilient cylindrical portion, a distal end of which is adapted to be received securely and sealingly within an open end of a distal first fluid conduit;
   b. a resilient tubular portion, a distal end of which meets a proximal end of said cylindrical portion, said tubular portion being coaxial with said cylindrical portion and having a bore adapted to receive, securely and sealingly, a blunt needle's hub therewithin;
   c. a self-sealing septum integral with said cylindrical and tubular portions, said septum having a channel therethrough adapted to receive, securely and sealingly, a blunt needle's needle portion.

10. An I.V. starting kit, comprising:
   a. a catheter portion, comprising:
      i. an elongate, substantially rigid, tubular cannula having a linear bore therethrough, a distal end of said cannula being open and blunt; and,
      ii. a hub securely affixed to a proximal end of said cannula, said hub having a bore coaxial with, and in fluid communication with, but with a diameter larger than that of, said cannula's bore;
   b. a coupling portion, comprising:
      i. a resilient cylindrical portion having a bore therethrough, a distal end of which is seated securely within said hub;
      ii. a resilient tubular portion, a distal end of which meets a proximal end of said cylindrical portion, said tubular portion having a bore which is coaxial with said hub's bore; and,
      iii. a pierceable, self-sealing septum integral with said cylindrical and tubular portions; and,
   c. a flesh piercing portion, comprising:
      i. a handle; and,
      ii. an elongate, rigid piercing element having a proximal end securely affixed to said handle and a distal end sharpened into a flesh piercing point, said piercing element having a diameter slightly less than the diameter of said cannula's bore and a length such that when said piercing element is driven through said coupling portion's septum and through said cannula's bore such that said handle meets said coupling portion's tubular portion, said piercing element's sharpened point protrudes a short distance beyond said cannula's open distal end.

11. The kit of claim 10, wherein said cylindrical portion is partially tubular.

12. The kit of claim 10, wherein said cylindrical portion is tubular at its distal end.

13. The kit of claim 10, wherein said piercing element is tubular.

14. The kit of claim 13, wherein said handle is hollow and has a bore in fluid communication with said tubular piercing element.

15. The kit of claim 14, wherein said handle has an open proximal end, and wherein a fluid-absorbent plug is secured in said handle's bore in said open proximal end.

16. The kit of claim 10, wherein said handle's distal end is shaped and dimensioned to seat securely and sealingly within said bore of said coupling portion's tubular portion.

17. The kit of claim 10, wherein said tubular portion's bore has a diameter larger than that of said cylindrical portion's bore.

18. The kit of claim 10, wherein said cylindrical portion is shaped and dimensioned for secure receipt within a female luer slip fitting.

19. The kit of claim 10, wherein said tubular portion is shaped and dimensioned for secure receipt of a male luer slip fitting.

20. The kit of claim 10, wherein said tubular portion is shaped and dimensioned for secure receipt of a male luer slip fitting having an axially and distally-extending needle portion.

21. A method for introducing an I.V. catheter into a vein while preventing blood from flowing from said I.V. catheter, wherein said I.V. catheter is comprised of a distal cannula and a proximal hub, comprising the steps of:
   a. lodging a resilient coupling in said hub, wherein said coupling comprises a resilient cylindrical portion, a distal end of which is adapted for secure, sealing receipt in said hub; a resilient tubular portion, a distal end of which meets a proximal end of said cylindrical portion, said tubular portion having a bore coaxial with said cylindrical portion; and, a pierceable, self-sealing septum integral with said cylindrical and tubular portions;
   b. driving piercing means axially through said tubular portion, through said septum, through said cylindrical portion, through said hub and through said cannula such that said piercing means projects from said cannula's distal end;

c. driving said piercing means and said cannula into said vein;

d. withdrawing said piercing means from said cannula, said hub, said cylindrical portion, said self-sealing septum and said tubular portion, whereby although blood flows into said catheter it is prevented from flowing beyond said self-sealing septum.

22. The method of claim 21, further including the step of engaging an element of I.V. apparatus with said coupling such that a hub of said element of I.V. apparatus seats securely and sealingly within said tubular portion's bore, and such that a needle portion of said element of I.V. apparatus breaches said septum, whereby a bore of said element of I.V. apparatus may be brought into fluid communication with a vein.

23. The method of claim 22, wherein said element of I.V. apparatus is a syringe having a heparin solution contained within its bore.

* * * * *